(12) United States Patent
Lins et al.

(10) Patent No.: US 12,018,971 B2
(45) Date of Patent: Jun. 25, 2024

(54) LIQUID LEVEL DETERMINATION

(71) Applicant: Bio-Rad Laboratories, Inc., Hercules, CA (US)

(72) Inventors: Adam Philip Lins, Martinez, CA (US); Glenn Leo Price, Martinez, CA (US); Robert Alan Iovanni, Vallejo, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 396 days.

(21) Appl. No.: 17/295,422

(22) PCT Filed: Dec. 3, 2019

(86) PCT No.: PCT/US2019/064205
§ 371 (c)(1),
(2) Date: May 19, 2021

(87) PCT Pub. No.: WO2020/117780
PCT Pub. Date: Jun. 11, 2020

(65) Prior Publication Data
US 2021/0404856 A1 Dec. 30, 2021

Related U.S. Application Data

(60) Provisional application No. 62/774,529, filed on Dec. 3, 2018.

(51) Int. Cl.
*G01F 23/292* (2006.01)
*G06F 16/245* (2019.01)
(Continued)

(52) U.S. Cl.
CPC .......... *G01F 23/292* (2013.01); *G06F 16/245* (2019.01); *G06T 7/62* (2017.01);
(Continued)

(58) Field of Classification Search
CPC ........ G01F 23/292; G01F 23/80; G01F 25/20; G06F 16/245; G06T 7/62; G06T 7/73;
(Continued)

(56) References Cited

U.S. PATENT DOCUMENTS

| 4,733,095 A | 3/1988 | Kurahashi et al. |
| 6,452,202 B1 | 9/2002 | Eom |

(Continued)

FOREIGN PATENT DOCUMENTS

| CN | 101509801 B1 | 10/2010 |
| CN | 204115819 U | 1/2015 |

(Continued)

OTHER PUBLICATIONS

US 9,134,161 B2, 09/2015, Walsh et al. (withdrawn)
(Continued)

*Primary Examiner* — Santiago Garcia
(74) *Attorney, Agent, or Firm* — Fenwick & West LLP

(57) ABSTRACT

Disclosed herein are a system and method for determining a liquid level in a container based on data extracted from a digital image of the container. An image capture apparatus captures an image of a container used to store liquid reagents used by analytical instruments to test patient samples. A controller receives the captured image and extracts an analysis region based on a container type and applies a gradient filter to the analysis region. A location of a minimum gradient value (i.e., a row index) is determined based on the air-to-liquid boundary of the liquid in the extracted analysis region. A volume module calculates the liquid level in the analysis region by dividing the row index by a length of a gradient column vector and compares the determined liquid level to a threshold analysis region fraction for the container type to determine whether to output an alert.

18 Claims, 10 Drawing Sheets

(51) Int. Cl.
    *G06T 7/62*  (2017.01)
    *G06T 7/73*  (2017.01)
    *G16H 10/40* (2018.01)
    *G16H 40/40* (2018.01)

(52) U.S. Cl.
    CPC ............... *G06T 7/73* (2017.01); *G16H 10/40* (2018.01); *G16H 40/40* (2018.01); *G06T 2207/10024* (2013.01); *G06T 2207/30004* (2013.01)

(58) Field of Classification Search
    CPC ........... G06T 2207/10024; G06T 2207/30004; G16H 10/40; G16H 40/40
    See application file for complete search history.

(56) References Cited

U.S. PATENT DOCUMENTS

| | | |
|---|---|---|
| 6,782,122 B1 | 8/2004 | Kline et al. |
| 6,993,176 B2 | 1/2006 | Yamagishi et al. |
| 7,499,581 B2 | 3/2009 | Tribble et al. |
| 7,728,873 B2 | 6/2010 | Segman |
| 7,982,201 B2 | 7/2011 | Bryant et al. |
| 8,184,848 B2 | 5/2012 | Wu et al. |
| 8,260,037 B2 | 9/2012 | Lin et al. |
| 8,381,581 B2 | 2/2013 | Walsh et al. |
| 8,644,547 B2 | 2/2014 | Hodder et al. |
| 9,002,096 B2 | 4/2015 | Pronkine |
| 9,068,875 B1 | 6/2015 | Wirthlin |
| 9,365,814 B2 | 6/2016 | Bachur, Jr. et al. |
| 9,446,418 B2 | 9/2016 | Johns et al. |
| 9,528,871 B2 | 12/2016 | Turner et al. |
| 9,541,445 B2 | 1/2017 | Tence et al. |
| 9,824,441 B2 | 11/2017 | Satish et al. |
| 9,846,070 B2 | 12/2017 | Omegna De Souza Filho |
| 9,910,054 B2 | 3/2018 | Johns |
| 9,915,675 B2 | 3/2018 | Arumugam et al. |
| 2003/0052288 A1 | 3/2003 | Calhoun |
| 2009/0067669 A1 | 3/2009 | Kojima |
| 2009/0107234 A1* | 4/2009 | Kim ................. G01F 23/80 73/293 |
| 2009/0153846 A1* | 6/2009 | Gan ................. G01F 23/292 356/133 |
| 2010/0086172 A1 | 4/2010 | Venkoparao et al. |
| 2012/0206595 A1* | 8/2012 | Alphenaar ......... G06Q 10/0631 702/45 |
| 2012/0314059 A1 | 12/2012 | Hoffmann et al. |
| 2014/0149265 A1 | 5/2014 | Kundra |
| 2015/0002658 A1 | 1/2015 | Jaw et al. |
| 2015/0033845 A1 | 2/2015 | Cacciola et al. |
| 2015/0130929 A1 | 5/2015 | Turner et al. |
| 2015/0130930 A1 | 5/2015 | Turner et al. |
| 2016/0116323 A1 | 4/2016 | Omegna De Souza Filho |
| 2016/0298997 A1 | 10/2016 | Tence et al. |
| 2016/0349278 A1 | 12/2016 | Johns et al. |
| 2017/0023395 A1 | 1/2017 | Guldalian |
| 2018/0023994 A1 | 1/2018 | Birtcher et al. |
| 2018/0045551 A1 | 2/2018 | Baker |
| 2018/0068460 A1 | 3/2018 | Huang et al. |
| 2018/0080871 A1* | 3/2018 | Imai ................. G01F 23/292 |
| 2018/0106659 A1 | 4/2018 | Kunbargi et al. |
| 2018/0108435 A1 | 4/2018 | Brown et al. |
| 2018/0306661 A1 | 10/2018 | Stacey |
| 2018/0330187 A1* | 11/2018 | Ouzounis .......... G06T 7/90 |
| 2018/0336433 A1 | 11/2018 | Nahum et al. |
| 2019/0078882 A1* | 3/2019 | Agata ............... G06T 7/20 |
| 2021/0209337 A1* | 7/2021 | Ozcan ............. G01N 33/1866 |
| 2021/0278268 A1* | 9/2021 | Hallgren .......... G01N 21/53 |

FOREIGN PATENT DOCUMENTS

| | | |
|---|---|---|
| CN | 105607661 A | 5/2016 |
| CN | 103743452 B1 | 8/2016 |
| CN | 205561965 U | 9/2016 |
| CN | 106197612 A | 12/2016 |
| CN | 106441493 A | 2/2017 |
| CN | 206177413 U | 5/2017 |
| CN | 107367766 A | 11/2017 |
| CN | 107462301 A | 12/2017 |
| CN | 206746572 U | 12/2017 |
| EP | 2133668 A1 | 12/2006 |
| EP | 2175420 A1 | 4/2010 |
| EP | 3144734 A1 | 3/2017 |
| EP | 3096109 B1 | 11/2017 |
| EP | 2131164 B1 | 1/2018 |
| JP | 3583659 B2 | 11/2004 |
| JP | 2007-078483 A | 3/2007 |
| JP | 2008-051570 A | 3/2008 |
| JP | 2012-514751 A | 6/2012 |
| JP | 5046972 B2 | 10/2012 |
| JP | 2018-040705 A | 3/2018 |
| NO | 20130453 A1 | 10/2014 |
| WO | WO 1999/067603 A1 | 12/1999 |
| WO | WO 2009/149933 A1 | 12/2009 |
| WO | WO 2010/080340 A1 | 7/2010 |
| WO | WO 2011/062352 A1 | 5/2011 |
| WO | WO 2017/114749 A1 | 7/2014 |
| WO | WO 2015/160997 A1 | 10/2015 |
| WO | WO 2017/051204 A1 | 3/2017 |
| WO | WO 2017/075153 A1 | 5/2017 |
| WO | WO 2017/166215 A1 | 10/2017 |
| WO | WO 2017/220630 A1 | 12/2017 |
| WO | WO 2018/105224 A1 | 6/2018 |

OTHER PUBLICATIONS

Eppel et al., "Computer vision-based recognition of liquid surfaces and phase boundaries in transparent vessels, with emphasis on chemistry applications," Nov. 6, 2014, arXiv:1404.7174v7, thirty-nine pages.

Gupta et al., "Sobel Edge Detection Algorithm," International Journal of Computer Science and Management Research, Feb. 2013, vol. 2, Issue 2, ISSN 2278-733X, pp. 1578-1583.

International Search Report and Written Opinion, Patent Cooperation Treaty Application No. PCT/US2019/064205, dated Mar. 24, 2020, nine pages.

Kabteyemer, M., "Automatic Monitoring of Liquid Level of Bottling Using Image Processing," [unpublished master's thesis] Haramaya University, Oct. 2015, fifty-nine pages.

Extended European Search Report, European Patent Office Application No. 19894199.9, dated Jun. 27, 2022, 9 pages.

First Office Action, China National Intellectual Property Administration Patent Application No. 201980079881.1, dated Oct. 20, 2021, 11 pages.

Second Office Action, China National Intellectual Property Administration Patent Application No. 201980079881.1, dated Mar. 16, 2022, 12 pages.

Rejection Decision, China National Intellectual Property Administration Patent Application No. 201980079881.1, dated Jun. 15, 2022, 5 pages.

Japanese Office Action, Japan Patent Office Patent Application No. 2021-531524, dated Sep. 20, 2023, 6 pages.

* cited by examiner

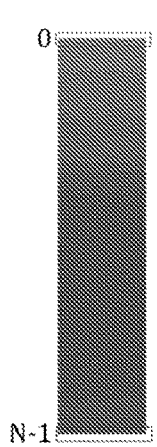
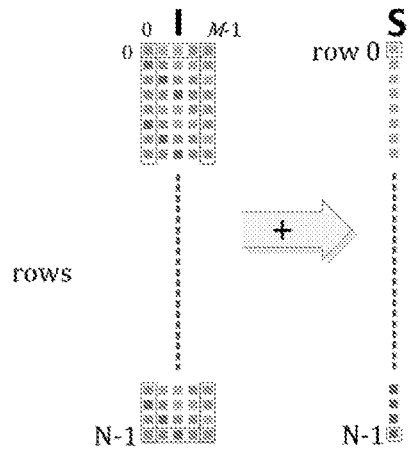
FIG. 6A  FIG. 6B  FIG. 6C
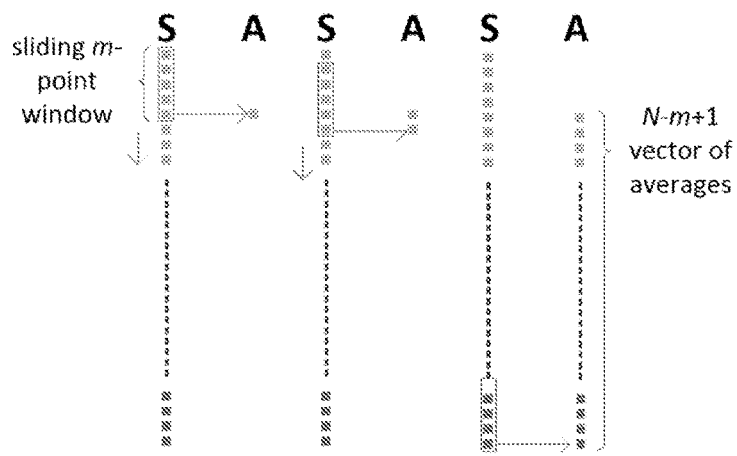
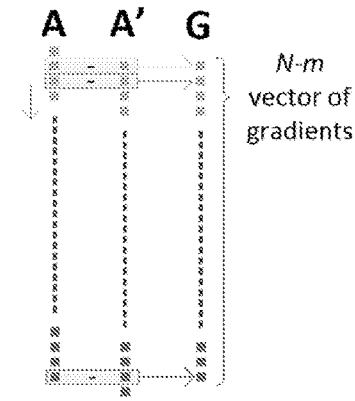
FIG. 6D  FIG. 6E liquid level

LIQUID LEVEL DETERMINATION

CROSS REFERENCE TO RELATED APPLICATIONS

This application is a 35 U.S.C § 371 Patent Application of PCT Application No. PCT/US2019/064205, filed on Dec. 3, 2019, which claims the benefit of U.S. Provisional Application No. 62/774,529, filed Dec. 3, 2018, both of which are incorporated by reference.

BACKGROUND

Automated analytical instruments or analyzers are used to test patient samples (e.g., blood or liquid) to determine if a patient suffers from a disease. The analyzers store reagents (e.g., buffers) in containers. The liquid level in the container is determined to ensure an adequate supply of reagent to complete the test(s). In some cases, inadequate liquid in the container can damage analyzer components.

One method to assess the volume of liquid in a container is by manual visual inspection by a human operator, which may be inaccurate and time-consuming. Electro-capacitive and pressure methods use a probe that contacts the liquid inside the container to determine the liquid level. However, such methods can result in contamination of the liquid in the container.

SUMMARY

Described herein are systems and methods for determining a liquid level in a container. The disclosure provides systems and methods that determine the liquid level in a container without contacting or contaminating the liquid. The systems and methods can be used in automated analytical instruments (e.g., automated blood analyzers).

BRIEF DESCRIPTION OF THE DRAWINGS

FIGS. 6A-6E show the steps in calculating a gradient of an analysis region according, to an embodiment. For clarity, not all the row and column pixels are shown in FIGS. 6B-6E.

DETAILED DESCRIPTION

Reference will now be made to several embodiments, examples of which are illustrated in the accompanying figures. It is noted that wherever practicable similar or like reference numbers are used in the figures to indicate similar or like functionality. One skilled in the art will readily recognize from the following description that alternative embodiments of the structures and methods may be employed without departing from the principles described.

Figure 1:
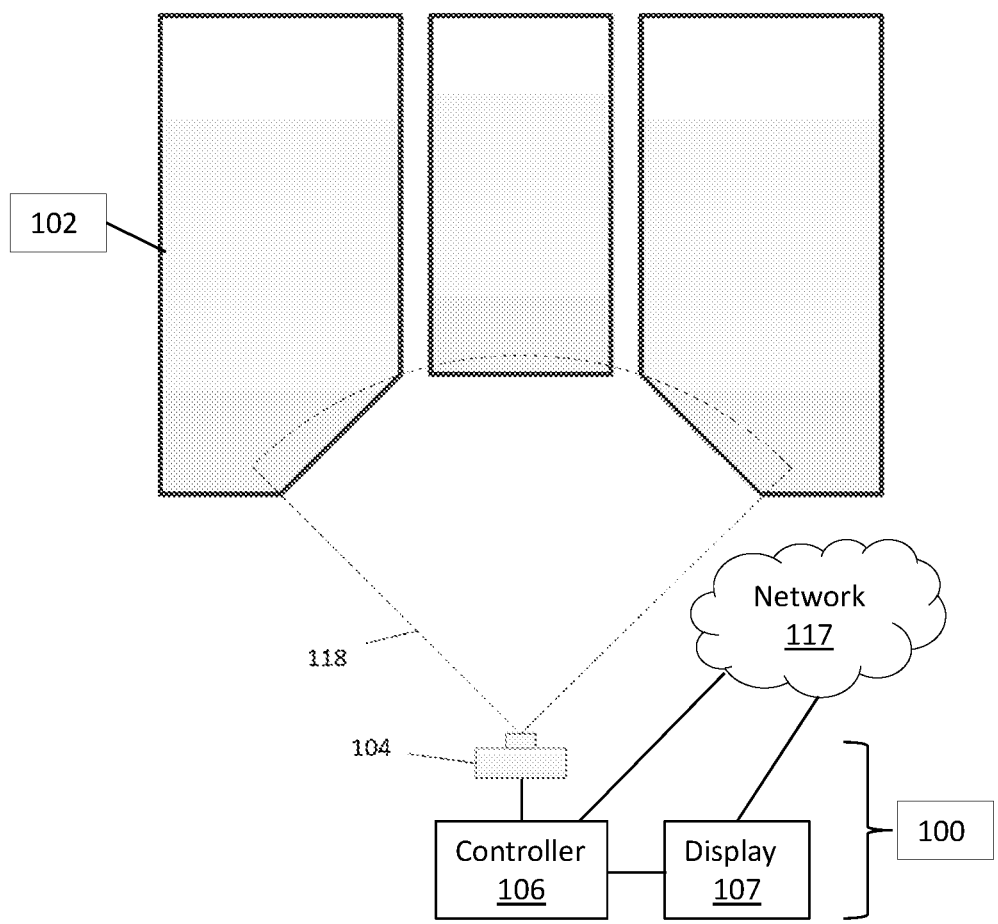
FIG. 1 is a block diagram illustrating a system for determining a liquid level in one or more containers, according to an embodiment.

Disclosed by way of example are a system and method for determining a liquid level in a container using an image capture apparatus and a controller. Turning now to FIG. 1, it illustrates one embodiment of a system 100 for determining a level of liquid in one or more containers 102 containing an unknown quantity of liquid. In the embodiment shown in FIG. 1, the system 100 includes an image capture apparatus 104, a controller 106, and a display 107. In other embodiments, the system 100 contains different and/or additional elements. In addition, the functions may be distributed among the elements in a different manner than described.

The container 102 is used to store liquid reagents that may be used by analytical instruments or analyzers to test patient samples, such as blood or other liquid. In one embodiment, the container 102 is formed from a translucent plastic material such as polypropylene, high density polyethylene, or polyvinyl chloride.

The image capture apparatus 104 is configured to capture digital images of one or more containers 102 and transmit the captured images to the controller 106 for analysis. In one embodiment, the image capture apparatus 104 includes an image sensor including a solid-state electronic device that captures light transmitted through a lens to form an image. Example sensor types include a charged coupled device (CCD) and a complementary metal-oxide-semiconductor (CMOS). The image capture apparatus 104 need not be complicated or expensive. The simpler digital cameras used in early generations of smartphones can be used. Lighting for the image capture apparatus 104 depends on the image sensor but can generally be similar to the ambient daytime lighting (e.g., visible light) of laboratory or office work spaces.

The controller 106 receives digital images of one or more containers 102 from the image captures apparatus 104, extracts an analysis region from the digital image, applies a gradient filter to the analysis region, determines a location of a minimum gradient value in the analysis region, and determines a liquid level in the container based on the determined minimum gradient value, as discussed below with respect to FIG. 5.

The display 107 receives information about the system 100 and determined liquid levels in the one or more containers 102 and outputs the received information for display to a user. In an embodiment, the display 107 is a component (along with the image capture apparatus 104 and controller 106) of an analytical analyzer (not shown) used to test patient samples, such as blood or other liquids. In some embodiments, the display 107 is remote from the system 100 and communicates with the controller 106 via the network 117. Example displays 107 remote from the system 100 include a smart phone, tablet, laptop computer, or desktop computer.

The system 100 is connected through a wired or wireless connection to the network 117. The network 117 is typically the Internet, but may be any network, including but not limited to a LAN, a MAN, a WAN, a mobile, wired or wireless network, telecommunication network, a private network, or a virtual private network, and any combination thereof. The network 117, if communicating within a room or a building and wirelessly, may use Bluetooth, near field communication, WiFi technologies, or similar methods of communication.

Figure 2:
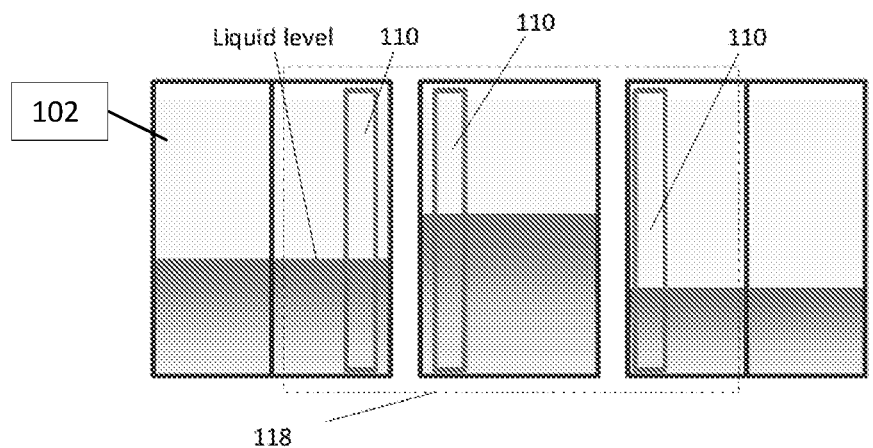
FIG. 2 is a schematic side view of the containers shown in FIG. 1, as seen by an image sensor of an image capture apparatus, according to an embodiment.

FIG. 2 is a schematic side view of the containers 102 shown in FIG. 1 as captured by an image sensor of the image capture apparatus 104, according to an embodiment. FIG. 2 also shows a field of view 118, which is a region detectable by the image capture apparatus 104. Within the field of view 118 are one or more analysis regions 110 used by the controller 106 to determine the liquid level in the container 102. In one embodiment, the field of view 118 of a digital image extends beyond the top and bottom of the container 102, as shown in FIG. 2.

Figure 3:
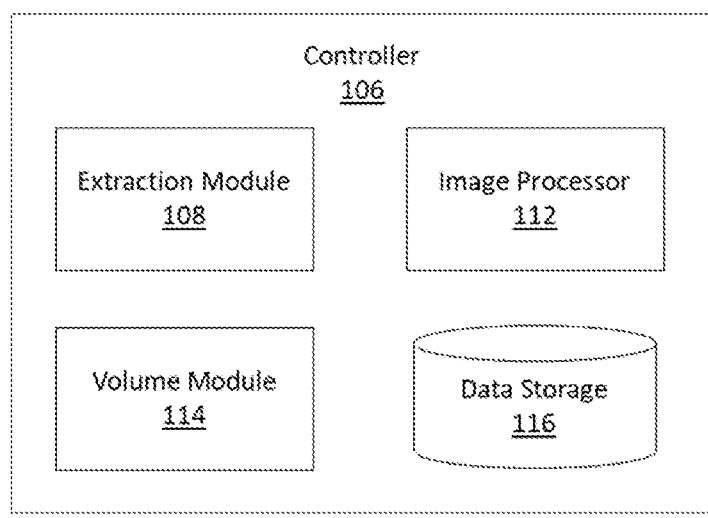
FIG. 3 is a block diagram illustrating a controller suitable for use in the system of FIG. 1, according to an embodiment.

FIG. 3 is a high-level block diagram of an embodiment of the controller 106. In various embodiments, the controller 106 is implemented as part of an embedded end-user application or as a program executing on a computer (e.g., a server-class computer) comprising a CPU, memory, network interface, and peripheral interfaces (e.g., a display, a keyboard), such as the computer shown in FIG. 13. The computer can run on an open-source operating system (e.g., LINUX) having a high-performance CPU, with 4GB or more of memory, and 32GB or more of disk storage. Other types of computers can be used, and it is expected that as more powerful computers are developed in the future, they can be configured in accordance with the teachings here. The functionality implemented by any of the elements can be provided from computer program products that are stored in non-transitory tangible computer accessible storage mediums (e.g., RAM, hard disk, or optical/magnetic media), or by equivalent implementations in hardware and/or firmware.

The controller 106 processes digital images from the image capture apparatus 104 by determining a liquid level in a container based on a minimum gradient value in an analysis region captured in a digital image of the container. In the embodiment shown in FIG. 3, the controller 106 includes an extraction module 108, an image processor 112, a volume module 114, and data storage 116.

The extraction module 108 is configured to extract an analysis region 110 from a digital image of the container 102. The image processor 112 is configured to process the analysis region 110 from the digital image. The volume module 114 is configured to calculate a volume fraction and/or a volume of liquid in the container 102. The functionality of these modules is discussed in more detail below with respect to FIG. 5.

Data storage 116 includes one or more non-transitory computer-readable media configured to store the digital image of the container 102 as well as information about the container 102, such as the type of container 102, a definition of the analysis region 110 for the container 102, and a cross-sectional volume of the container 102. Data storage 116 can be volatile (e.g., RAM) or non-volatile (e.g., a hard drive). In one embodiment, data storage 116 is remote from the system 100 and accessed via the network 117. Alternatively, data storage 116 is a native component of the system 100. In some embodiments, the data is stored using techniques such as lookup tables to improve the speed and/or reliability of access.

Figure 4:
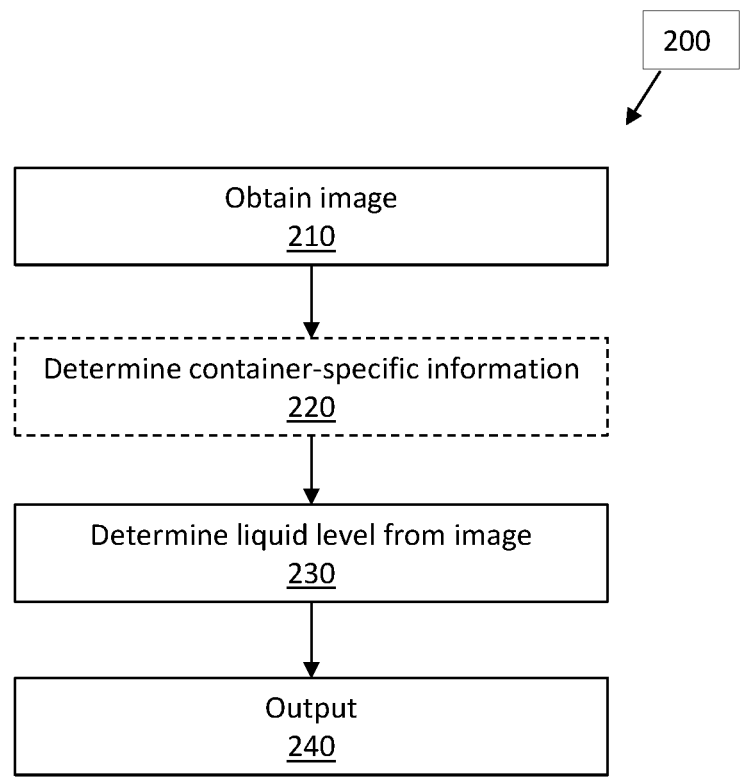
FIG. 4 is a flow chart illustrating a method of determining a liquid level in a container, according to an embodiment.

FIG. 4 illustrates a method 200 of determining a liquid level of a container 102, according to an embodiment. The steps of FIG. 4 are illustrated from the perspective of the controller 102 performing the method 200. However, some or all of the steps may be performed by other entities or components. In addition, some embodiments may perform the steps in parallel, perform the steps in different orders, or perform different steps.

In the embodiment shown, the controller 106 obtains 210 an image of the container 102 from the image capture apparatus 104. If the controller 106 can determine the liquid level of multiple types of containers 102, the controller 106 determines 220 the type(s) of container(s) 102 using container-specific information, as discussed below with respect to FIG. 5. The controller 106 can receive information about the type of container 102 in many ways, including, for example, by visible indicia on the image, by an RFID tag on the container 102, or a signal from one or more physical switches in the container holder. In an alternate embodiment, the controller 106 does not determine the container type.

The controller 106 determines 230 the liquid level from the image, as discussed below with respect to FIG. 5, and outputs 240 the liquid level of the container 102 (e.g., through the display 107). Additionally, in some embodiments, the controller 106 alters the operation of the instrument or takes other corrective action based on the determined liquid level of the container 102. For example, if the liquid level is below a threshold, the controller 106 may trigger display of a warning to a user, switch the instrument into a liquid-saving operation mode, submit a requisition or maintenance request for more of the liquid, or the like.

Figure 5:
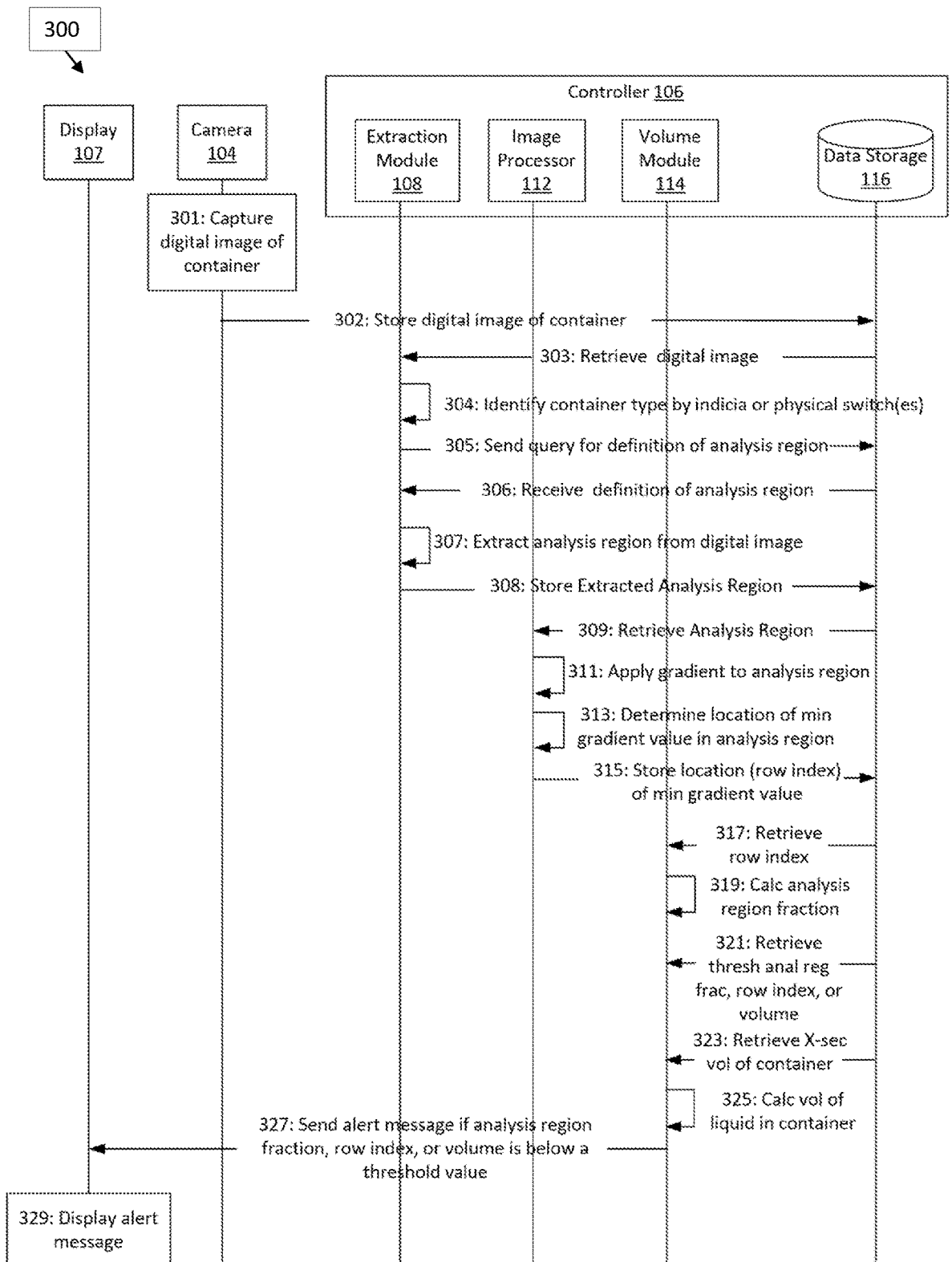
FIG. 5 is a sequence diagram illustrating a method of determining a liquid level in a container, according to an embodiment.

FIG. 5 illustrates a computer-implemented method 300 of determining a volume fraction of liquid in a container 102, according to one embodiment. The steps of FIG. 5 are illustrated from the perspective of various elements of the system 100 performing the method 300. However, some or all of the steps may be performed by other entities or components. In addition, some embodiments may perform the steps in parallel, perform the steps in different orders, or perform different steps.

In one embodiment, the controller 106 initiates the method 300 responsive to receiving user input requesting an instrument performs a test that uses a liquid stored in one or more of the containers 102. In some implementations, execution of the test is based on an amount of liquid in the container 102. For example, the controller 106 instructs the image capture apparatus 104 to capture an image of the container 102 and compares the captured image to a liquid threshold. If the controller 106 determines, based on the captured image, that the amount of liquid in the container 102 is equal to or exceeds the threshold amount, the controller 106 determines (and optionally, outputs an indication) that the test may proceed. Conversely, if the amount of liquid in the container 102 is less than the threshold amount, the controller 106 outputs an indication that the test has been halted and that the container should be replaced or refilled.

In alternate configurations, the method 300 runs at startup of the instrument, periodically at a configurable rate, after each test, or after a pre-determined number of tests (e.g., after two or more tests) regardless of an amount of liquid in the container 102.

The image capture apparatus 104 captures 301 a digital image of the container 102 and sends 302 the digital image to data storage 116. In one embodiment, the digital image is a grayscale image. Alternatively, if the digital image is a color image, the image processor 112 may convert the color image to grayscale prior to analysis.

In one embodiment, the extraction module 108 retrieves 303 the digital image from data storage 116 and identifies 304 the type of container 102 in the image. For example, a minimum field of view 118 within the image includes one or more analysis regions 110 and optionally, visible indicia on the container 102 or a container holder (e.g., a barcode). In embodiments where the system detects liquid levels for more than one container or type of container, the indicia can identify the container type in the image. In some embodiments, in which one or more fixed types of containers are used, the indicia identifying the type of container(s) is stored in data storage 116 separate from the digital image of the container 102 captured by the image capture apparatus 104. The indicia may be an identifier used to retrieve information (e.g., a definition of the analysis region, cross-sectional volume, container type, alarm thresholds) stored in data storage 116 about the container 102. This information is used when multiple types/sizes of containers 102 are analyzed allowing the computed liquid level to depend on the identified container characteristics (e.g., two containers that differ only in length have different total internal volumes).

In an alternate embodiment, containers are not identified visually, but rather using a signal triggered by a physical switch. For example, when the container 102 is placed in the container holder, the container 102 presses on or otherwise activates one or more physical switches and causes an electrical circuit for each switch to be completed or closed. A small-sized container can activate one switch, a medium-sized container can activate two switches, and a large-sized container can activate three switches. In another example, a unique pattern of switches is activated for each type of container. The number or pattern of switches activated for each container type is stored in data storage 116 and may be retrieved by the controller 106 for use in identifying the container 102 (e.g., if the container 102 cannot be identified visually). In some embodiments, the container holder is also configured to match a footprint of a specific container type.

Alternatively, in embodiments in which the container type is known, the type of container is pre-stored in data storage 116. Based on the indicia or the one or more activated physical switches, the extraction module 108 queries 305 the data storage 116 for a definition (e.g., location or boundaries) of an analysis region 110 of the container 102 in the digital image. In some embodiments, the analysis region 110 is based in part on a container type and is defined by x- and y-coordinates of two corners of the analysis region 110. Alternatively, the analysis region 110 is defined by the x- and y-coordinate of one of the corners of the analysis region 110 along with a width and height of the analysis region 110. The extraction module 108 receives 306 the definition of the analysis region 110 and extracts 307 the analysis region 110 from the digital image. In some embodiments, the analysis region 110 is between about 1-50 pixels wide and about 70-90% of the height of the container 102 in the image. In some embodiments, the analysis region 110 is one pixel wide. The extraction module 108 stores 308 the extracted analysis region 110 in the data storage 116.

The image processor 112 retrieves 309 the extracted analysis region 110 (as shown in FIGS. 6A and 6B; N×M matrix, I, of intensities) from the data storage 116. In an embodiment, the image processor 112 sums the row-wise intensities (as shown in FIG. 6C; N×1 vector S), computes the column-wise sliding averages of intensities in the extracted analysis region 110 (as shown in FIG. 6D; column vector A), and computes a first-order derivative or a gradient of the averages (as shown in FIG. 6E; gradient G). When summing the row-wise intensities, each element in S is the sum of the values in the corresponding row in I. When computing the column-wise sliding averages of pixels in the extracted analysis region 110, column vector A is created by using a sliding m-point window to average the rows in S. In some embodiments, m is equal to two or more (e.g., two to ten). Each element in A is the average of m values in S. The vector A has m−1 fewer elements than S. The gradient G is computed by element-wise subtraction of the rows of A. For example, gradient G can be computed by subtracting row p-k from row p, for k≤p<(N−m). In some embodiments, the row-wise intensities of the pixels are not summed prior to computing the column-wise sliding averages and the gradient of the sliding averages is summed along the x-axis. When the analysis region 110 is one pixel wide, the image processor 112 computes the column-wise sliding averages of pixels in the extracted analysis region 110 without first summing the row-wise intensities.

In some embodiments, the image processor 112 applies 311 a gradient filter (such as a Sobel filter or a Sobel-Feldman operator) to the analysis region 110 to extract a Sobel gradient. The gradient filter performs a 2D spatial gradient measurement on the digital image and emphasizes regions of high spatial frequency that correspond to edges in the images (i.e., areas with strong intensity contrasts between pixels). In some embodiments, the image processor 112 averages the pixels along the x-axis and extracts the Sobel gradient along the y-axis. Alternatively, the image processor 112 extracts the Sobel gradients along the y-axis and sums the extracted gradients along the x-axis in the analysis region 110.

Figure 7:
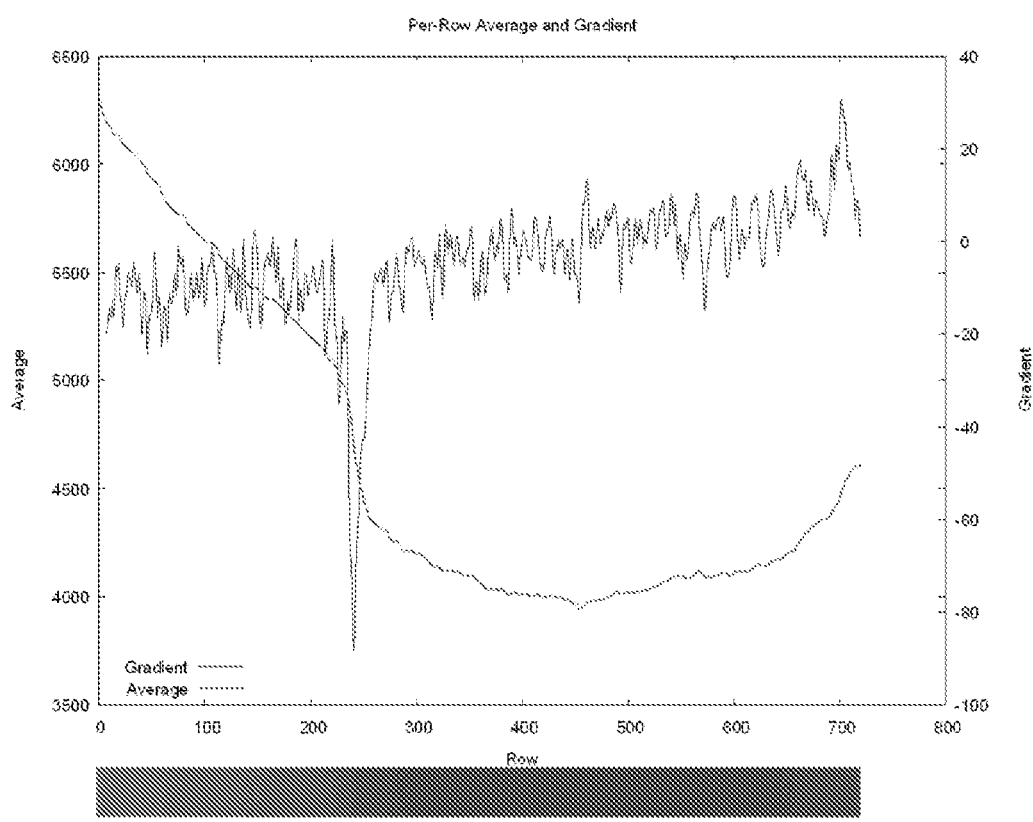
FIG. 7 shows an example averaged intensity and gradient vector plotted as a function of row index with the initial analysis region of a digital image below the x-axis, according to an embodiment. The plot shows the point of minimum gradient that clarifies the location of the air-to-liquid boundary or meniscus.

Next, the image processor 112 determines 313 a location of a minimum gradient value in the extracted analysis region 110. The location of the minimum gradient value occurs at the air-to-liquid boundary (i.e., the meniscus) of the liquid in the extracted analysis region 110 (that is, if the meniscus is in the extracted analysis region 110). The location of the minimum gradient value is determined by searching along the vector of gradient values, i.e., by searching for a row index or pixel row in a column vector that contains the minimum value (as shown in FIG. 7). Note that when the level of the liquid is above or below the analysis region 110, the gradient values will be relatively constant across the row indexes. In an embodiment in which the Sobel filter is applied to pixels along the y-axis, and the extracted Sobel gradients are summed along the x-axis, the location of the minimum gradient value is determined by searching along the vector of summed Sobel gradient values. In an embodiment in which the image processor 112 averages the pixels along the x-axis and applies the Sobel filter along the y-axis, the location of the minimum gradient value is determined by searching along the vector of the extracted Sobel gradient. The image processor 112 stores 315 the location (i.e., the row index) of the minimum gradient value, which is the location of the liquid level in the analysis region 110, in data storage 116.

Figure 8:
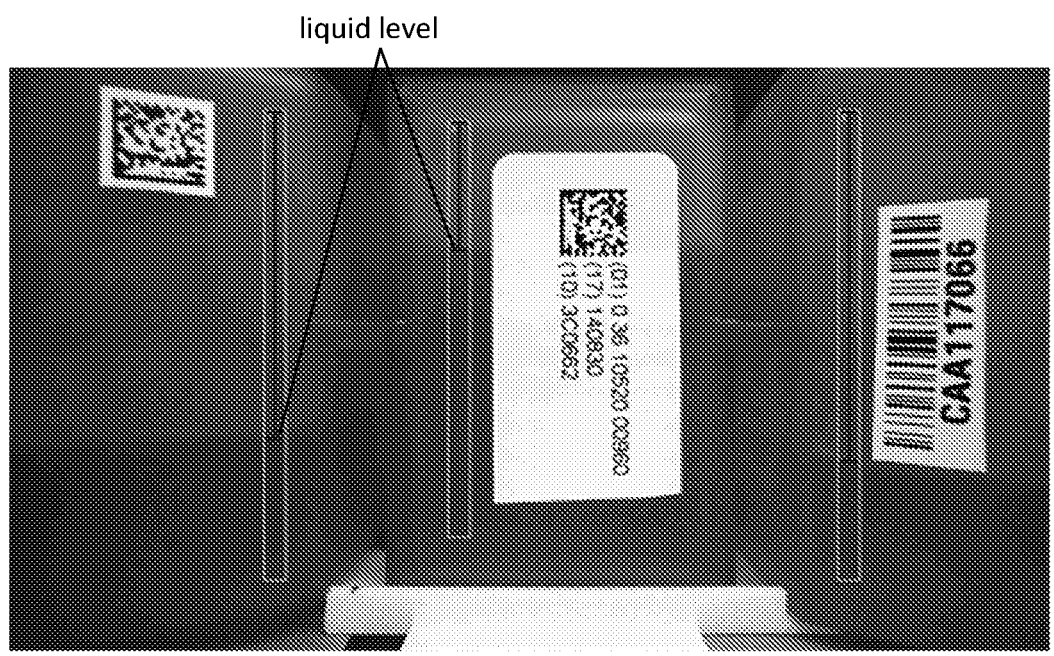
FIG. 8 shows an original digital image with the analysis regions and results of liquid level measurement overlaid on the digital image, according to an embodiment.

The volume module 114 retrieves 317 the row index from data storage 116 and calculates 319 a fraction of liquid (i.e., the liquid level) in the analysis region 110 or an analysis region fraction (as shown in FIG. 8). In an embodiment, the analysis region fraction is calculated by dividing the row index by the length of the gradient column vector. The volume module 114 retrieves 321 from data storage 116 a threshold analysis region fraction for the container 102 based on an identifier associated with the container type. The threshold analysis region fraction indicates the level of liquid at or below which an alert is sent to the display 107. For example, the alert might indicate that the instrument should not operate when the liquid is below a specified level, request that additional fluid be added to reduce instrument down time, or the like. The volume module 114 compares the determined analysis region fraction associated with the container type with the retrieved threshold analysis region fraction. In one embodiment, if the determined analysis region fraction for the container type is below the retrieved threshold, the volume module 114 sends an alert to the display 107. Alternatively, the volume module 114 does not calculate an analysis region fraction and instead retrieves 321 a threshold row index for the container based on an identifier associated with the container type and compares the determined row index to the retrieved threshold row index. An alert is sent to the display 107 based on the comparison of the determined row index to the threshold index.

In yet another embodiment, the volume module 114 determines the volume of liquid in the container 102 by retrieving 323 a cross-sectional volume of the container 102 from data storage 116 based on the container type. In embodiments in which the container 102 shape varies, the cross-sectional volume of the container will also vary. Thus, for containers in which the shape varies, the volume module 114 retrieves multiple cross-sectional volumes. When data storage 116 receives a query from the volume module 114, data storage 116 uses the container type to retrieve the container cross-sectional volume (s). The volume module 114 then calculates 325 the volume of liquid in the container 102 by summing the cross-sectional volumes between the location of the minimum gradient value (i.e., row index) and the end of the analysis region 110 and adding a constant volume (also stored based on the container indicia) to account for the liquid below the analysis region 110. If the calculated volume of liquid is below the threshold volume, an alert is sent.

The volume module 114 sends 327 the alert for display 329 on the display 107. The alert can be a message in text, an icon, or any other visual indication. The alert can also be an audible alert, e.g., a chime or klaxon. Additionally or alternatively, an alert may be presented in locations other than on the display 107. For example, a warning light on an automated analyzer instrument may be activated. In some embodiments, in addition to or in place of an alert, the instrument will not operate further until the volume module 114 determines that the volume of the container 102 is above the threshold. Responsive to the volume fraction, row index, or volume being above the threshold analysis region fraction, row index, or volume, a prior requested operation of the instrument proceeds. In some embodiments, the display 107 includes a status of the liquid level or volume of the container 102. Such a status is updated with the determined analysis volume fraction or volume. Furthermore, in some embodiments, the alert causes an operational parameter of the instrument 100 to be changed (e.g., to reduce an amount of liquid used), a requisition or order for additional fluid to be sent, or triggering of any other appropriate preventative maintenance action for the instrument.

In certain embodiments, the image processor 112 uses the gradient of the averaged pixels in the analysis region 110 to determine if a container 102 is absent or missing. An object or shape with a well-defined edge is placed behind the container 102 so that when the container 102 is absent, the object or shape will be in the analysis region 110 when a digital image is captured. For example, in an embodiment, one or more white bars or a container holder with distinct edges is visible in the background when the container 102 is absent. When the gradient for the analysis region 110 is calculated, it will have a different shape due to the object or shape in the analysis region 110.

Figure 9:
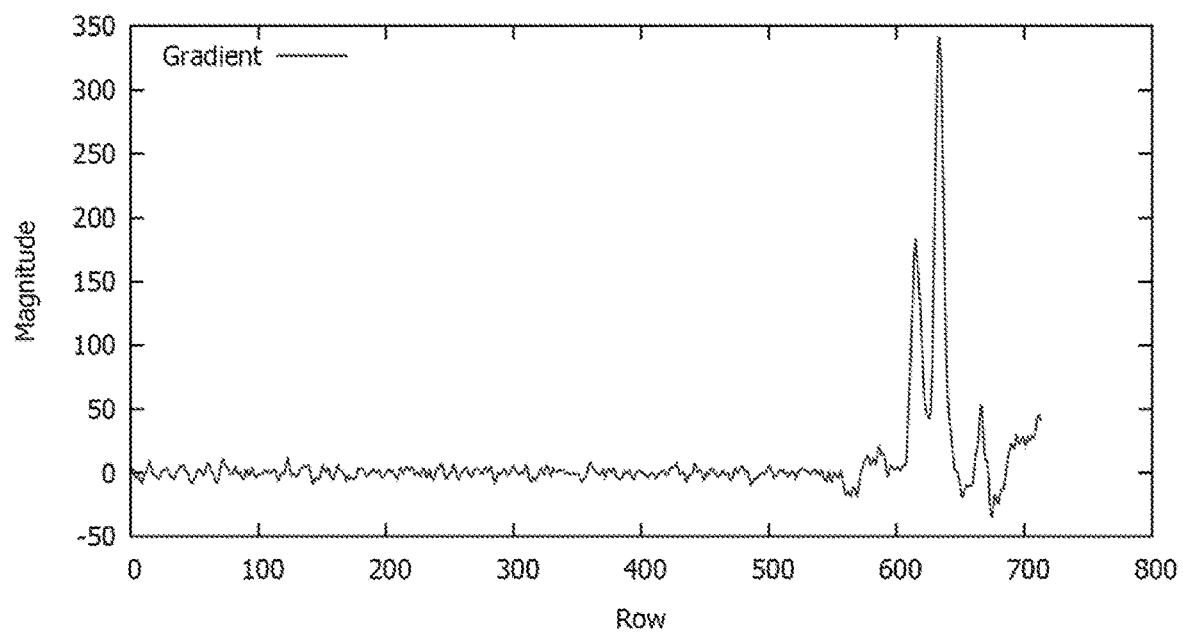
FIG. 9 shows an example gradient vector plot for an analysis region in which a container is missing, according to an embodiment. The gradient has a strong positive peak due to an edge from a container holder shown in FIG. 10.
Figure 10:
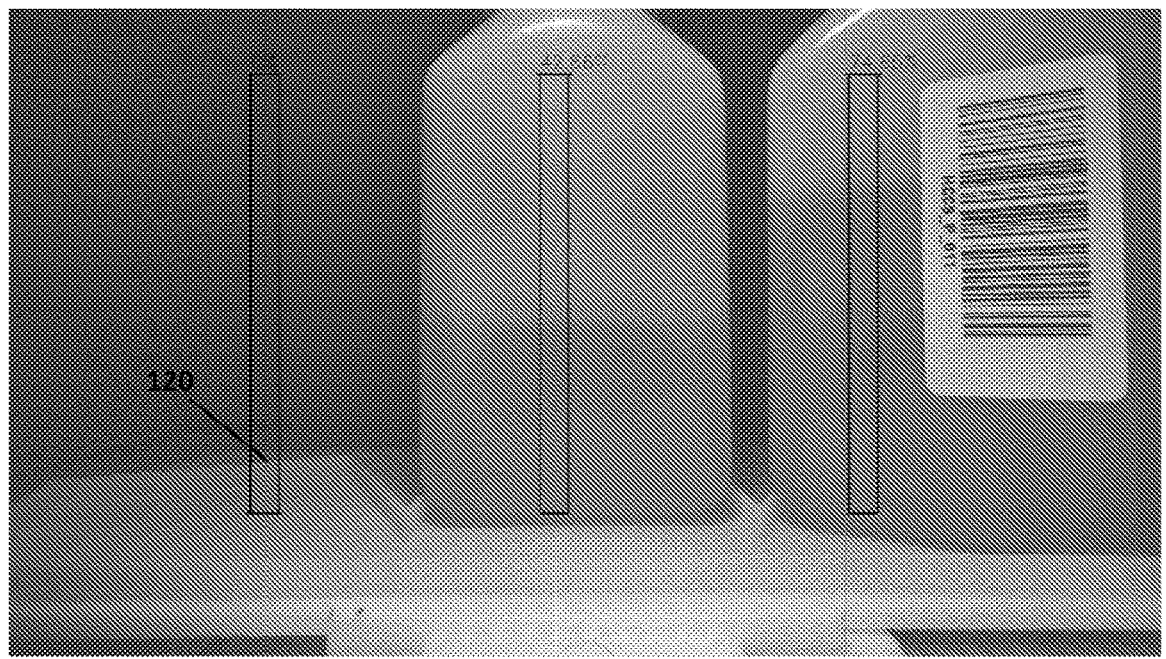
FIG. 10 shows an original digital image of a set of containers in which one container is absent, according to an embodiment. Analysis regions and results of liquid level measurement are overlaid on the digital image.
Figure 11:
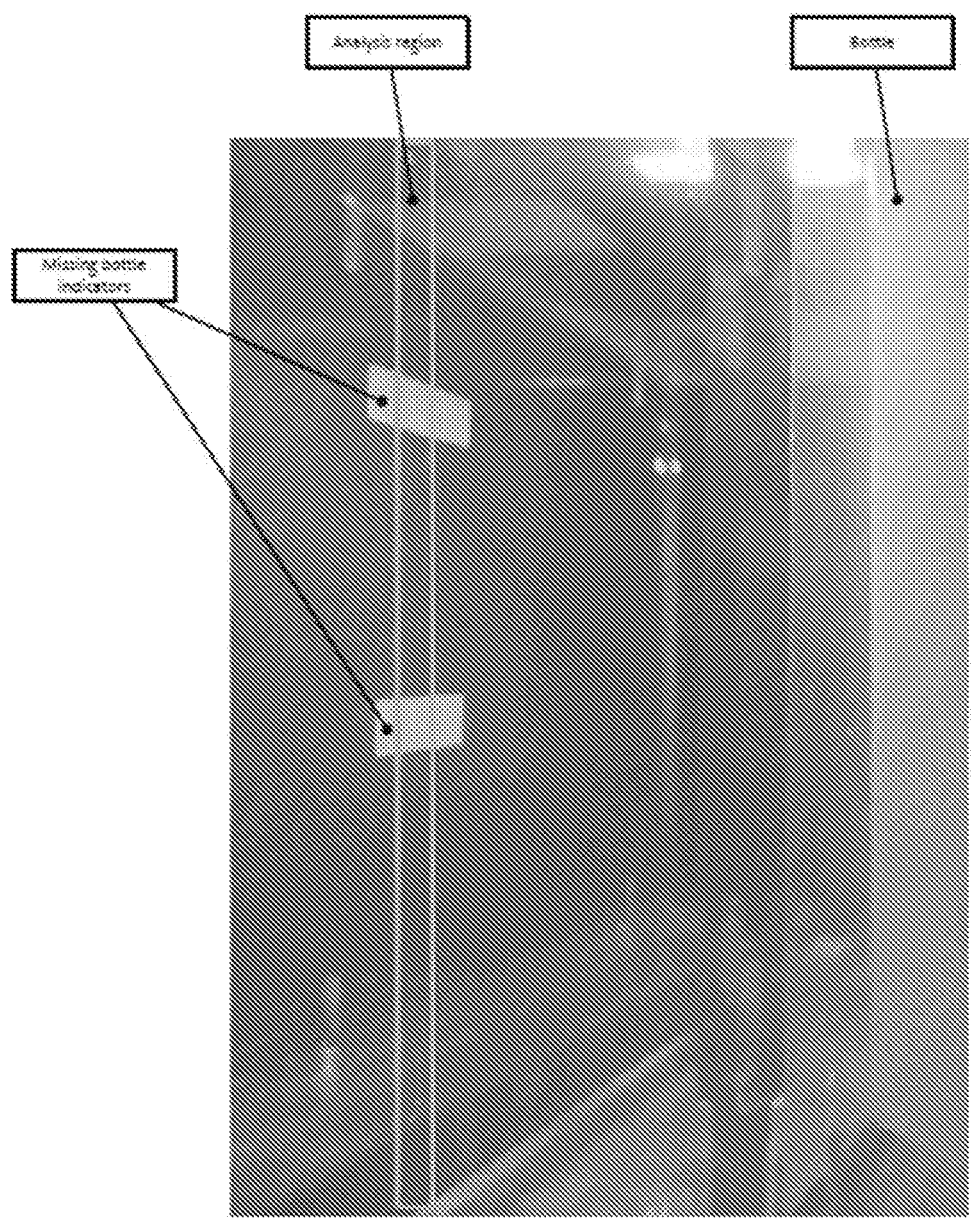
FIG. 11 shows a digital image in which white bars are placed in the background of the analysis region when the container is absent.
Figure 12:
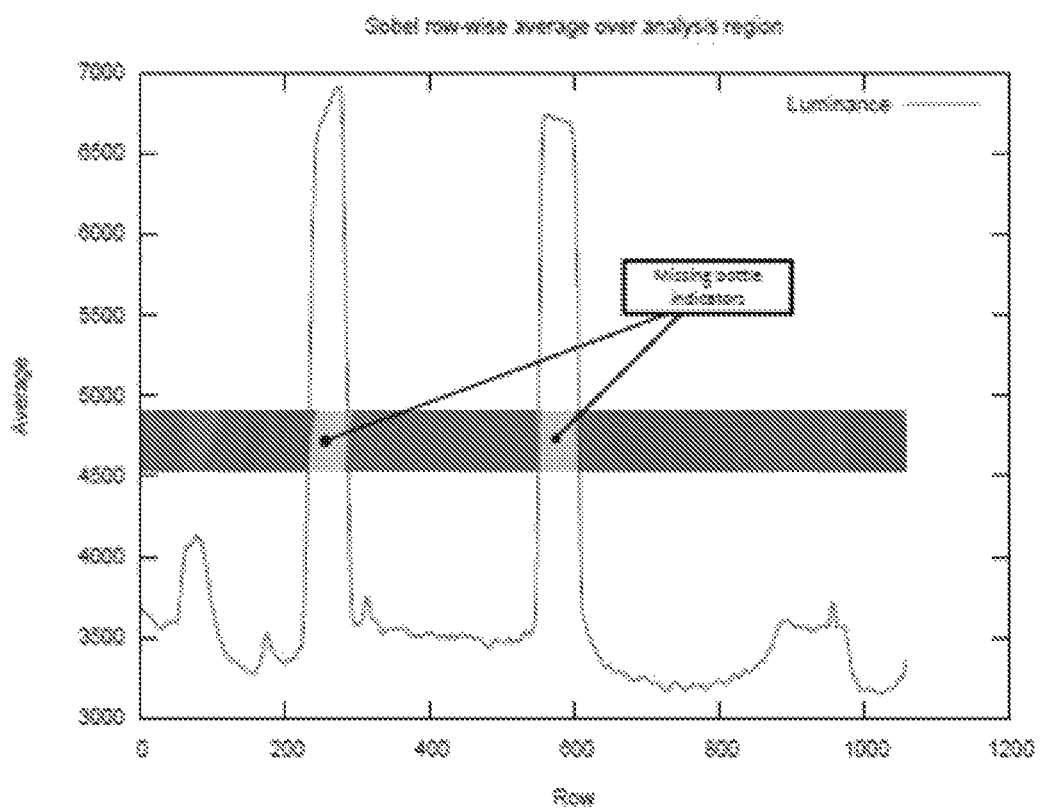
FIG. 12 shows an example gradient vector plot in which the gradient has a strong peak corresponding to the locations of the white bars within the analysis region.

In an embodiment in which a container holder has a bright and well-defined edge 120 (such as the edge 120 shown in FIG. 10) that is visible when the container 102 is absent from the container holder, the gradient has a strong positive peak (i.e., a maximum gradient value as shown in FIG. 9) instead of a negative peak (or minimum gradient value) due to the well-defined edge 120 of the container holder (as shown in FIG. 10). When present, the container 102 blocks the edge 120 of the container holder. In an embodiment in which white bars are placed in the background of the analysis region 110, when the container 102 is absent (as shown in FIG. 12), the gradient has a strong peak corresponding to the locations of the white bars within the analysis region 110 (as shown in FIG. 11). Independent of or simultaneous with the image processor 112 searching along the vector of gradient values for a minimum gradient value (to determine the liquid level), the image processor 112 can search along the vector of gradient values for one or more maximum gradient values. Responsive to identifying the presence of a maximum gradient value (or a strong positive gradient peak), the image processor 112 sends an alert that the container 102 is absent. Optionally, responsive to the presence of a maximum gradient value, the controller 106 outputs a volume of zero.

Figure 13:
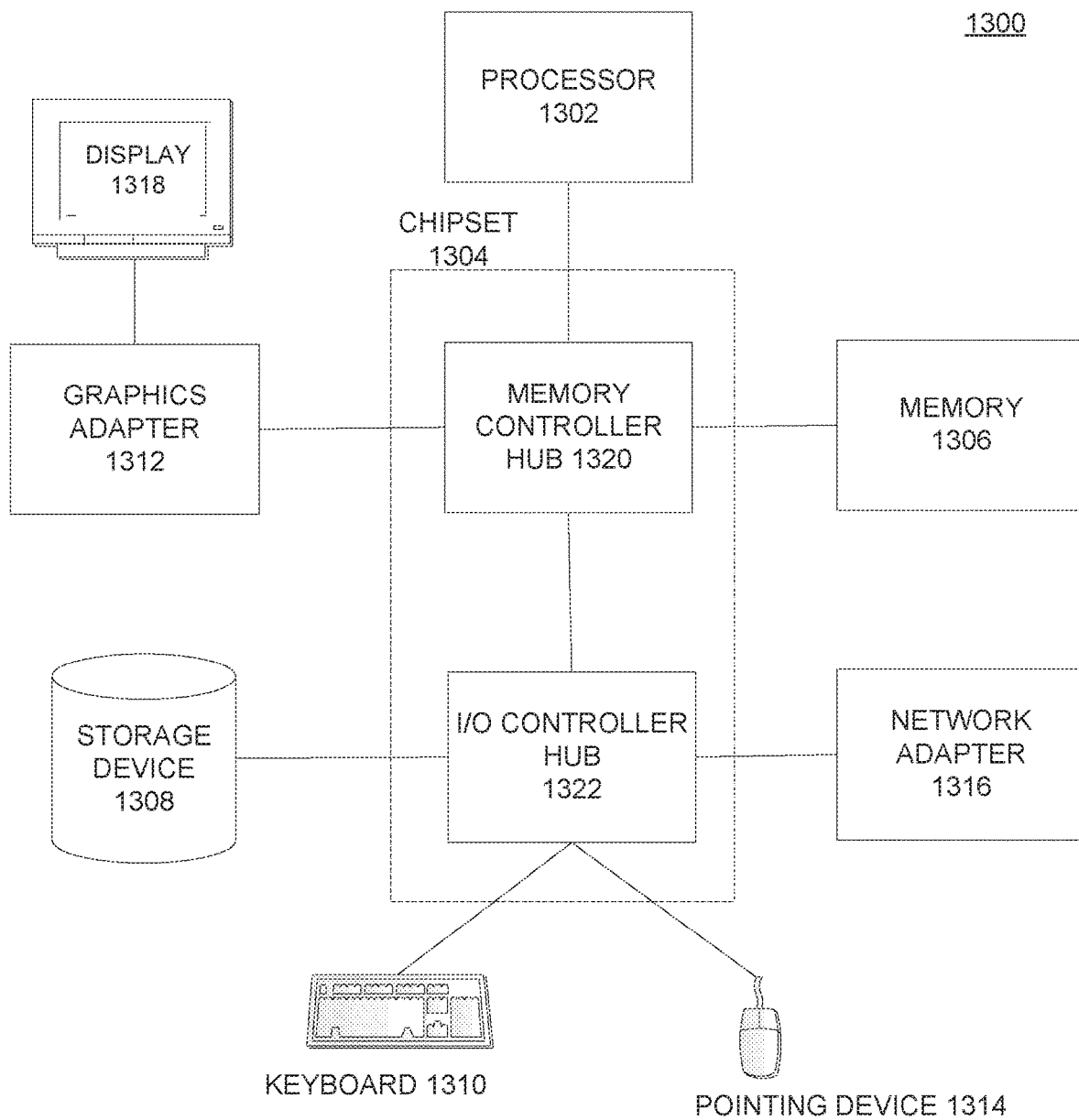
FIG. 13 is a block diagram illustrating example components of a computer used as part or all of the system, according to an embodiment.

FIG. 13 is a block diagram illustrating physical components of a computer 1300 used as part or all of the system 100 of FIG. 1, in accordance with an embodiment. Illustrated are at least one processor 1302 coupled to a chipset 1304. Also coupled to the chipset 1304 are a memory 1306, a storage device 1308, a graphics adapter 1312, and a network adapter 1316. A display 1318 is coupled to the graphics adapter 1312. In one embodiment, the functionality of the chipset 1304 is provided by a memory controller hub 1320 and an I/O controller hub 1322. In another embodiment, the memory 1306 is coupled directly to the processor 1302 instead of the chipset 1304.

The storage device 1308 is any non-transitory computer-readable storage medium, such as a hard drive, compact disk read-only memory (CD-ROM), DVD, or a solid-state memory device. The memory 1306 holds instructions and data used by the processor 1302. The graphics adapter 1312 displays images and other information on the display 1318. The network adapter 1316 couples the computer 1300 to a local or wide area network.

As is known in the art, a computer 1300 can have different and/or other components than those shown in FIG. 13. In addition, the computer 1300 can lack certain illustrated components. In one embodiment, a computer 1300, such as a host or smartphone, may lack a graphics adapter 1312, and/or display 1318, as well as a keyboard 1310 or external pointing device 1314. Moreover, the storage device 1308 can be local and/or remote from the computer 1300 (such as embodied within a storage area network (SAN)).

As is known in the art, the computer 1300 is adapted to execute computer program modules for providing functionality described herein. As used herein, the term "module" refers to computer program logic utilized to provide the specified functionality. Thus, a module can be implemented in hardware, firmware, and/or software. In one embodiment, program modules are stored on the storage device 1308, loaded into the memory 1306, and executed by the processor 1302.

In sum, the approaches disclosed enable a computer-based system to automatically detect the level of liquid in a container. These approaches may be implemented without the addition of a probe or any other physical component inside the container 102, reducing the likelihood of liquid contamination. This enables greater automation and efficiency in the operation of various instruments by enabling computer-based systems to monitor liquid levels in a way of which they were previously not capable. Furthermore, these approaches are not analogous to the techniques previously used by humans.

The foregoing description has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe embodiments in terms of algorithms and symbolic representations of operations on information. These algorithmic descriptions and representations are commonly used by those skilled in the data processing arts to convey the substance of their work effectively to others skilled in the art. These operations while described functionally computationally or logically are understood to be implemented by computer programs or equivalent electrical circuits microcode or the like. Furthermore, it has also proven convenient at times to refer to these arrangements of operations as modules without loss of generality. The described operations and their associated modules may be embodied in software firmware hardware or any combinations thereof.

Any steps, operations, or processes described herein may be performed or implemented with one or more hardware or software modules alone or in combination with other devices. In one embodiment a software module is implemented with a computer program product comprising a computer-readable medium containing computer program code which can be executed by a computer processor for performing any or all of the steps operations or processes described.

Embodiments may also relate to an apparatus for performing the operations herein. This apparatus may be specially constructed for the required purposes and/or it may comprise a general-purpose computing device selectively activated or reconfigured by a computer program stored in the computer. Such a computer program may be stored in a non-transitory tangible computer readable storage medium or any type of media suitable for storing electronic instructions which may be coupled to a computer system bus. Furthermore, any computing systems referred to in the specification may include a single processor or may be architectures employing multiple processor designs for increased computing capability.

Embodiments may also relate to a product that is produced by a computing process described herein. Such a product may comprise information resulting from a computing process where the information is stored on a non-transitory tangible computer readable storage medium and may include any embodiment of a computer program product or other data combination described herein.

As used in this specification and the appended claims, the singular forms "a", "an", and "the" include plural references unless the content clearly dictates otherwise.

All patents, patent applications, and other published reference materials cited in this specification are hereby incorporated herein by reference in their entirety.

Finally, the language used in the specification has been principally selected for readability and instructional purposes, and it may not have been selected to delineate or circumscribe the inventive subject matter. It is therefore intended that the scope of the invention be limited not by this detailed description but rather by any claims that issue on an application based hereon. Accordingly, the disclosure of the embodiments of the invention is intended to be illustrative but not limiting of the scope of the invention which is set forth in the following claims.

What is claimed is:

1. A system for determining a level of liquid in a container, the system comprising:
    an image capture apparatus; and
    a controller configured to:
        receive a digital image of a container from the image capture apparatus, the container containing an unknown quantity of liquid;
        extract an analysis region from the digital image;
        calculate gradient values for different positions in the analysis region, wherein calculating gradient values comprises:
            summing a plurality of row-wise pixel intensities in the analysis region,
            computing a column-wise average of pixel intensities in the analysis region, and
            for each row, computing a column-wise gradient value by computing an element wise subtraction of rows of the column-wise averages;
        identify a minimum gradient value of the gradient values; and
        determine a level of liquid in the container based on the position of the minimum gradient value in the analysis region.

2. The system of claim 1, wherein the digital image is a color image and wherein the controller is further configured to convert the color image to grayscale.

3. The system of claim 1, wherein the controller being configured to extract an analysis region from the digital image comprises the controller being configured to:
    identify one or more visible indicia in the digital image;
    query a data store for a container type associated with the identified visible indicia; and
    identify a location of the analysis region in the digital image based on the container type.

4. The system of claim 1, wherein the controller being configured to calculate gradient values for different positions in the analysis region comprises the controller being configured to:
    apply a Sobel filter to pixels along a y-axis of the analysis region to extract a Sobel gradient; and
    sum the extracted Sobel gradients along the x-axis of the analysis region.

5. The system of claim 1, wherein the analysis region has a width of one pixel and wherein the controller being configured to calculate gradient values comprises the controller being configured to compute a row-wise intensity gradient of pixels along a y-axis of the analysis region.

6. The system of claim 1, wherein the controller being configured to determine a level of liquid in the container comprises the controller being configured to compute a fraction of liquid in the analysis region by dividing a row index by a length of a gradient column vector in the analysis region.

7. The system of claim 1, wherein the controller is further configured to:
compare the determined liquid level to a threshold level associated with a container type; and
responsive to determining that the liquid level is below the threshold level associated with the container type, outputting an alert to a display device.

8. The system of claim 1, wherein the controller is further configured to determine a volume of liquid in the container based on the liquid level and a stored cross-sectional volume of the container.

9. The system of claim 1, wherein the controller is further configured to:
compare the determined liquid level to a threshold level associated with a container type; and
responsive to determining that the liquid level is below the threshold level associated with the container type, switching an automated analyzer to a liquid-saving operation mode.

10. A computer-implemented method for determining a level of liquid in a container, the method comprising:
receiving a digital image of the container from an image capture apparatus, the container containing an unknown quantity of liquid;
extracting an analysis region from the digital image;
calculating gradient values for different positions in the analysis region, wherein calculating gradient values comprises:
summing a plurality of row-wise pixel intensities in the analysis region,
computing a column-wise average of pixel intensities in the analysis region, and
for each row, computing a column-wise gradient value by computing an element wise subtraction of rows of the column-wise averages;
identifying a minimum gradient value of the gradient values; and
determining a level of liquid in the container based on the position of the minimum gradient value in the analysis region.

11. The method of claim 10, wherein the digital image is a color image and the method further comprises converting the color image to grayscale.

12. The method of claim 10, wherein extracting an analysis region from the digital image comprises:
identifying one or more visible indicia in the digital image;
querying a data store for a container type associated with the identified visible indicia; and
identifying a location of the analysis region in the digital image based on the container type.

13. The method of claim 10, wherein calculating gradient values for different positions in the analysis region comprises:
applying a Sobel filter to pixels along a y-axis of the analysis region to extract a Sobel gradient; and
summing the extracted Sobel gradients along the x-axis of the analysis region.

14. The method of claim 10, wherein the analysis region has a width of one pixel and wherein calculating gradient values comprises computing a row-wise intensity gradient of pixels along a y-axis of the analysis region.

15. The method of claim 10, wherein determining a level of liquid in the container comprises computing a fraction of liquid in the analysis region by dividing a row index by a length of a gradient column vector in the analysis region.

16. The method of claim 10, further comprising:
comparing the determined liquid level to a threshold level associated with a container type; and
responsive to determining that the liquid level is below the threshold level associated with the container type, outputting an alert to a display device.

17. The method of claim 10, further comprising determining a volume of liquid in the container based on the liquid level and a stored cross-sectional volume of the container.

18. The method of claim 10, further comprising:
comparing the determined liquid level to a threshold level associated with a container type; and
responsive to determining that the liquid level is below the threshold level associated with the container type, switching an automated analyzer to a liquid-saving operation mode.

* * * * *